(12) United States Patent
Keri et al.

(10) Patent No.: US 7,683,188 B2
(45) Date of Patent: Mar. 23, 2010

(54) PROCESS FOR PREPARATION OF MYCOPHENOLIC ACID AND ESTER DERIVATIVES THEREOF

(75) Inventors: Vilmos Keri, Debrecen (HU); Zoltan Czovek, Debrecen (HU)

(73) Assignee: TEVA Gyógyszergyár Zártkörüen Müködö Részvénytársaság, Debrecen (HU)

(*) Notice: Subject to any disclaimer, the term of this patent is extended or adjusted under 35 U.S.C. 154(b) by 335 days.

(21) Appl. No.: 11/115,819

(22) Filed: Apr. 26, 2005

(65) Prior Publication Data

US 2005/0250952 A1     Nov. 10, 2005

Related U.S. Application Data

(60) Provisional application No. 60/572,527, filed on May 18, 2004, provisional application No. 60/565,694, filed on Apr. 26, 2004.

(51) Int. Cl.
   *C07D 307/00* (2006.01)
(52) U.S. Cl. .................................. 549/302; 544/153
(58) Field of Classification Search ................ 549/302; 544/153
   See application file for complete search history.

(56) References Cited

U.S. PATENT DOCUMENTS

| | | | |
|---|---|---|---|
| 4,115,197 A | 9/1978 | Queener et al. | |
| 4,452,891 A | 6/1984 | Kida et al. | |
| 4,748,173 A | 5/1988 | Nelson et al. | |
| 4,753,935 A | 6/1988 | Nelson et al. | |
| 4,786,637 A | 11/1988 | Allison et al. | |
| 4,808,592 A | 2/1989 | Nelson et al. | |
| 4,861,776 A | 8/1989 | Nelson et al. | |
| 4,868,153 A | 9/1989 | Allison et al. | |
| 4,948,793 A | 8/1990 | Allison et al. | |
| 4,952,579 A | 8/1990 | Nelson et al. | |
| 5,247,083 A | 9/1993 | Knox et al. | |
| 5,455,045 A | 10/1995 | Samuels et al. | |
| 5,543,408 A | 8/1996 | Fu et al. | |
| 5,545,637 A | 8/1996 | Fu et al. | |
| 5,688,529 A | 11/1997 | Lidgate et al. | |
| 6,107,052 A | 8/2000 | Dorn | |
| 6,172,107 B1 | 1/2001 | Haeberlin et al. | |
| 6,225,073 B1 | 5/2001 | Alexander et al. | |
| 6,306,900 B1 | 10/2001 | Haeberlin et al. | |
| 6,333,198 B1 | 12/2001 | Edmeades et al. | |
| 6,709,846 B1 | 3/2004 | Sircar et al. | |
| 6,927,047 B1 | 8/2005 | Sircar et al. | |
| 7,122,687 B2 | 10/2006 | Poornaprajna et al. | |
| 7,138,504 B2 | 11/2006 | Bodepudi et al. | |
| 2004/0167130 A1 | 8/2004 | Lee et al. | |
| 2005/0085635 A1 | 4/2005 | Chudik et al. | |
| 2005/0165243 A1 | 7/2005 | Poornaprajna et al. | |
| 2006/0035297 A1 | 2/2006 | Bodepudi et al. | |
| 2007/0032483 A1 | 2/2007 | Greil et al. | |

FOREIGN PATENT DOCUMENTS

| | | |
|---|---|---|
| EP | 0 281 713 | 9/1988 |
| EP | 0 963 980 | 12/1999 |
| GB | 1 157 099 | 7/1969 |
| GB | 1 158 387 | 7/1969 |
| GB | 1158387 | 7/1969 |
| HU | 210 262 A | 7/1995 |
| JP | 55-019055 A | 2/1980 |
| JP | 56-127093 A | 10/1981 |
| JP | 57-022693 A | 2/1982 |
| JP | 59-091891 A | 5/1984 |
| WO | WO 94/01427 | 1/1994 |
| WO | WO-96/02004 A1 | 1/1996 |
| WO | WO 97/38689 | 10/1997 |
| WO | WO 00/34503 | 6/2000 |
| WO | WO-00/75363 A2 | 12/2000 |
| WO | WO 01/21607 | 3/2001 |
| WO | WO 01/64931 | 9/2001 |
| WO | WO 02/100855 | 12/2002 |
| WO | WO-03/042393 A1 | 5/2003 |
| WO | WO-03/106690 A1 | 12/2003 |
| WO | WO 2004/020426 | 3/2004 |
| WO | WO 2004/064806 | 8/2004 |
| WO | WO 2004/087174 A1 | 10/2004 |
| WO | WO-2005/014567 A1 | 2/2005 |
| WO | WO-2005-033089 A1 | 4/2005 |
| WO | WO-2005/039552 A2 | 5/2005 |
| WO | WO-2005/042507 A1 | 5/2005 |
| WO | WO-2005/105771 A1 | 11/2005 |
| WO | WO-2006/024582 A1 | 3/2006 |
| WO | WO-2006/038218 A1 | 4/2006 |
| WO | WO-2006/076802 A1 | 7/2006 |
| WO | WO-2008/026883 A1 | 3/2008 |
| ZA | 68/4959 | 11/1967 |

OTHER PUBLICATIONS

Covarrubias-Zuniga et al., Analytical Sciences (2000), 16(7), 783-784.*
Harrison et al., 2000, CAS: 77:126344.*
Alexis Biochemicals, Alexis corporation, Web sit updated in 2008.*

(Continued)

*Primary Examiner*—Rei-tsang Shiao
(74) *Attorney, Agent, or Firm*—Kenyon & Kenyon LLP

(57) ABSTRACT

Provided are processes for preparation of mycophenolic acid.

10 Claims, 4 Drawing Sheets

OTHER PUBLICATIONS

Fermentek biotechnology, Wet Site updated in 2009.*

Rihs et al., "Metal-Organic Compounds: Sodium Mycophenolate", *Acta Crystallographic* 2000, C56, pp. 423-433.

Wrigglesworth et al. "Analogues of Capsaicin with Agonist Activity as Novel Analgesic Agents: Structure-Activity Studies", *Journal of Medicinal Chemistry*, 1996, pp. 4942-4951, vol. 39, No. 25.

Caira, "Crystalline Polymorphism of Organic Compounds", *Topics in Current Chemistry*, 1998, pp. 163-208. vol. 198.

Sadhukhan et al. "Optimization of Mycophenolic Acid Production in Solid State Fermentation Using Response Surface Methodology", *Journal of Industrial Microbiology and Biotechnology*, 1999, pp. 33-38, vol. 22, No. 1.

Makara et al. "Nuclear Magnetic Resonance and Molecular Modeling Study on Mcyophenolic Acid: Implications for Binding to Inosine Monophosphate Dehydrogenase", *Journal of Medicinal Chemistry*, 1996, pp. 1236-1242. vol. 39, No. 6+.

Abraham, "The Effect Of Mycophenolic Acid On The Growth Of Staphylococcus Aureus In Heart Broth", *Biochem. J.*, 1945, pp. 398-408. vol. 39, No. 5.

Ando, et al., "Antiviral Activity Of Mycophenolic Acid Studies On Antiviral And Antitumor Antibiotics. IV", *The Journal of Antibiotics*, Aug. 19, 1968, pp. 649-652, vol. 21, No. 11.

Bentley, "Bartolomeo Gosio, 1863-1944: An Appreciation", *Advances In Applied Microbiology*, 2001, pp. 229-251, vol. 48.

Bentley, "Mycophenolic Acid: A One Hundred Year Odyssey From Antibiotic To Immunosuppressant", *Chem. Rev.* 2000, pp. 3801-3825, vol. 100, No. 10.

Guillory, "Polymorphism in Pharmaceutical Solids", *Drugs and the Pharmaceutical Sciences*, edited by Brittain, 1999, pp. 184-222, vol. 95, Marcel Dekker, Inc.

Clutterbuck, et al., "The Metabolic Products Of The Penicillium Brevi-Compactum Series", *Studies In The Biochemistry Of Micro-Organisms*, 1932, pp. 1441-1458.

Craig, et al., "The Relevance Of The Amorphous State To Pharmaceutical Dosage Forms: Glassy Drugs And Freeze Dried Systems", *International Journal of Pharmaceutics*, 1999, pp. 179-207, vol. 179.

Desrosiers, et al., "High Throughput Screening Techniques For Pre-Formulation: Salt Selection And Polymorph Studies", *Acta Cryst.*, 2002, A58 (Supplement), C9.

Filtenborg, et al., "Simple Screening Method For Molds Producing Intracellular Mycotoxins In Pure Cultures", *Applied and Environmental Microbiology*, Feb. 1983, pp. 581-585, vol. 45, No. 2.

Franklin, et al., "The Inhibition Of Nucleic Acid Synthesis By Mycophenolic Acid", *Biochem. J.*, 1969, pp. 515-524, vol. 113.

Frisvad, et al., "Classification Of Terverticillate Penicillia Based On Profiles Of Mycotoxins And Other Secondary Metabolites", *Applied and Environmental Microbiology*, 1983, pp. 1301-1310, vol. 48, No. 6.

Gainer, et al., "GLC Of Mycophenolic Acid And Related Compounds", *Journal of Pharmaceutical Sciences*, 1970, pp. 1157-1159, vol. 59, No. 8.

Gilliver, "The Inhibitory Action Of Antibiotics On Plant Pathogenic Bacteria And Fungi", Annals of Botany, N. S., 1946, pp. 271-282, vol. 10, No. 39.

Gosio, "Sur La Reconnaissance De L'Arsenic, Au Moyen De Certaines Moisissuree", *Archives Italiennes Do Biologie*, 1893. pp. 299-305.

Gu, at al., "Grouping Solvents By Statistical Analysis Of Solvent Property Parameters: Implication To Polymorph Screening", *International Journal of Pharmaceutics*, 2004, pp. 117-125, vol. 283.

Gu, et al., "Polymorph Screening: Influence Of Solvents On The Rate Of Solvent-Mediated Polymorphic Transformation", *Journal of Pharmaceutical Sciences*, 2001, pp. 1878-1890, vol. 90, No. 11.

Hilfiker, et al., "Polymorphism—Integrated Approach From High-Throughput Screening To Crystallization Optimization", *Journal of Thermal Analysis and Calorimetry*, 2003, pp. 429-440, vol. 73.

Makara, et al., "Nuclear Magnetic Resonance And Molecular Modeling Study On Mycophenolic Acid: Implications For Binding To Monophosphate Dehydrogenase", *Journal of Medicinal Chemistry*, 1996, pp. 1236-1242, vol. 39, No. 6.

Noto, et al., "Some Biological Properties Of Mycophenolic Acid", *The Journal of Antibiotics*, 1969, pp. 165-169, vol. 22, No. 4.

Nowak, et al., "Mycophenolic Acid Binding To Human Serum Albumin: Characterization and Relation To Pharmacodynamics", *Clinical Chemistry*, 1995, pp. 1011-1017, vol. 41, No. 7.

Rihs, et al.. "Sodium Mycophenolate", *Acta Crystallographica*, 2000, pp. 432-433, vol. C56.

Snyder, et al., *Introduction to Modem Liquid Chromatography*, $2^{nd}$ *Ed.*, 1979, pp. 549-572, John Wiley & Sons, Inc.

Sollinger, Hans W., "Mycophenolate Mofetil", *Kidney International*, 1995. pp. S-14-S-17, vol. 48, Suppl. 52.

Strobel, et al., *Chemical Instrumentation: A Systematic Approach*, $3^{rd}$ *Ed.*, 1989, pp. 391-393, 879-894, 922-925, 953.

Wagner, et al., "Carboxylic Esters", *Synthetic Organic Chemistry*, 1953, pp. 479-531.

Wiwattanawongsa, et al., "Determination Of Mycophenolic Acid And Its Phenol Glucuronide Metabolite In Human Plasma And Urine By High-Performance Liquid Chromatography", *Journal of Chromatography B*, 2001, pp. 35-45, vol. 763.

International Search Report dated Jul. 28, 2008, issued during prosecution of PCT/US2008/004724.

Bedford, C.T., et al., "Biosynthesis of mycophenolic acid", Can. J. Chem., 1973, vol. 51, pp. 694-697.

Canonica, L., et al., "Biosynthesis of mycophenolic acid", J. Chem. Soc., 1972, vol. 21, pp. 2639-2643.

Detroy, R.W., et al., "Relationship between the biosynthesis of virus-like particles and mycophenolic acid in *Penicillium stoloniferum* and *P. brevi-compactum*", Can. J. Microbiol., 1973, vol. 19, pp. 1459-1462.

Colombo, Lino, et al., "6-Farnesyl-5, 7-dihydroxy-4-methylphthalide Oxidation Mechanism in Mycophenolic Acid Biosynthesis", J. Chem. Soc., 1982, vol. 2, pp. 365-373.

ICH Harmonised Tripartite Guideline, "Good Manufacturing Practice Guide for Active Pharmaceutical Ingredients", Q7A, Current Step 4 Version, Nov. 10, 2000.

Johnson, I.S., "Pharmaceuticals containing mycophenolic acid for treatment of psoriasis", Chem. Abstr. 1972, vol. 77, pp. 92853.

Gainer, Frank E., et al., "GLC of Mycophenolic Acid and Related Compounds", Journal of Pharmaceutical Sciences, Aug. 1970, vol. 59, No. 8, pp. 1157-1159.

Muth, W.L., et al., "Biosynthesis of mycophenolic acid: Purification and characterization of S-adenosyl-L-methionine: demethylmycophenolic acid O-methyltransferase", Antimicrob. Agents Chemother., 1975, vol. 8. pp. 321-327.

Neely, F.L., et al., "High-performance liquid chromatographic determination of mycophenolic acid in fermentation broth", J. Chromatogr., 1991, vol. 540, pp. 383-385.

Noto, T., et al., "A turbidimetric bioassay method for determination of mycophenolic acid", 1970, J. Antibiot., vol. 23, p. 96-98.

Nulton, C.P., et al., "Labelled acetone and levulinic acid are formed when [14C] acetate is being converted to mycophenolic acid in *Penicillium brevicompactum*", 1978, Can. J. Microbiol., vol. 24, pp. 199-201.

Ozaki, H., et al., "Mycophenolic acid production by drug-resistant and methionine or glutamic-acid requiring mutants of *Penicillium brevicompactum*", Agric. Biol. Chem., 1987, vol. 51, pp. 2509-2514.

Pastore, A., et al., "Rapid determination of mycophenolic acid in plasma by reversed-phase high-performance liquid chromatography", J. Chromatogr., 2002, vol. 776, pp. 251-254.

* cited by examiner

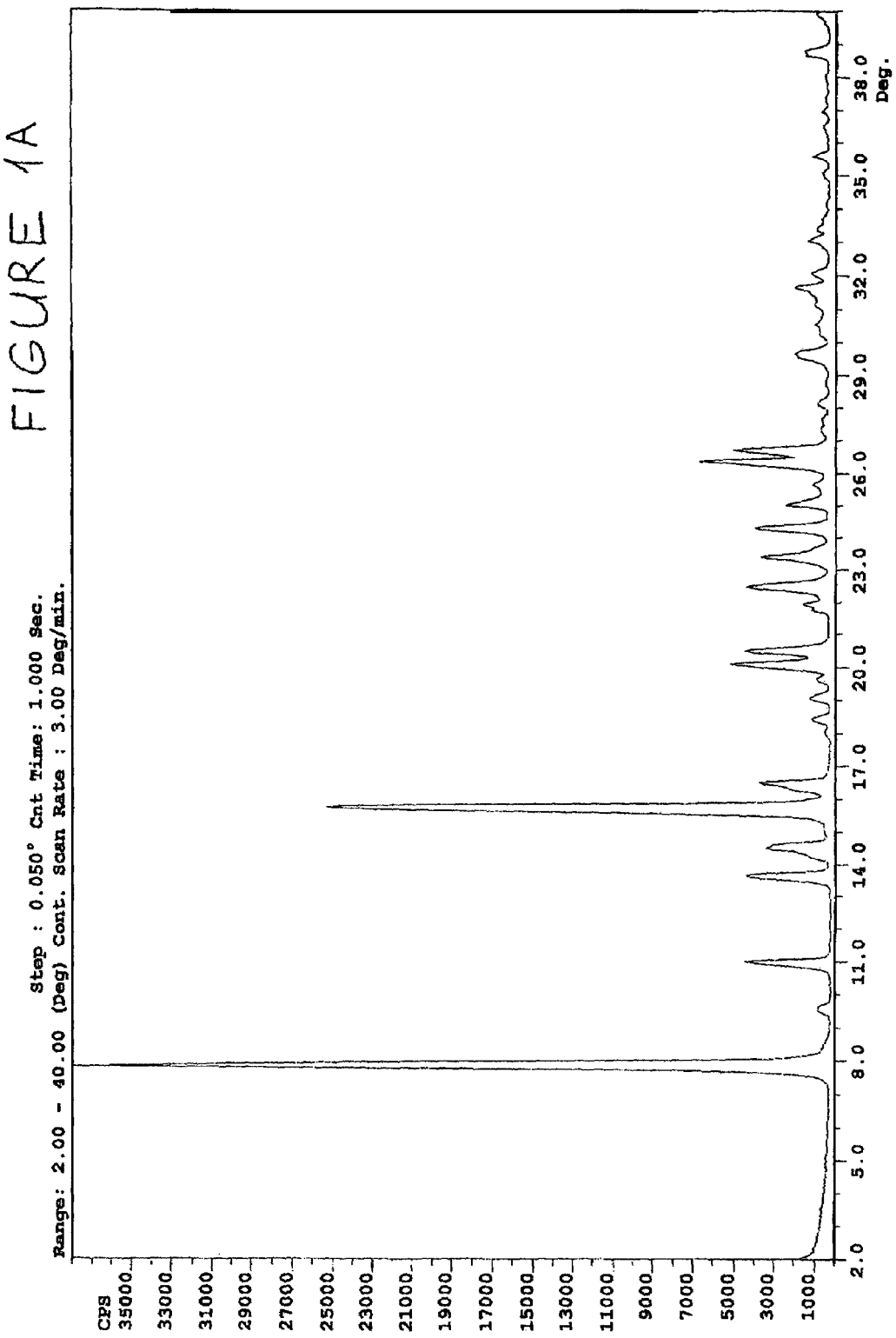

FIGURE 1B

D:\Thermo ARL\datafiles\samples\Mycophenol sav2\

| Position (Deg.) | Position (Dsp.) | Corr.Fact | Intensity (CPS) | Rel. Int. (%) | FWHM (L) (Deg.) | Area (CPS·Deg.) | Strain (%) | CSize (Å) | CSize source |
|---|---|---|---|---|---|---|---|---|---|
| 11.2734 | ...3358 | 0.0000 | 24582.10 | 100.00 | 0.2054 | 8236.5 | 0.00 | 0.00 | None |
| 9.2467 | ...5569 | 0.0000 | 425.27 | 1.73 | 0.2397 | 166.2 | 0.00 | 0.00 | None |
| 8.0661 | ...9598 | 0.0000 | 2767.78 | 11.26 | 0.2042 | 921.7 | 0.00 | 0.00 | None |
| 6.5013 | ...6089 | 0.0000 | 2832.75 | 11.52 | 0.2220 | 1025.7 | 0.00 | 0.00 | None |
| 6.1048 | ...4973 | 0.0000 | 1914.14 | 7.79 | 0.2971 | 927.5 | 0.00 | 0.00 | None |
| 5.6454 | ...6844 | 0.0000 | 17398.01 | 70.78 | 0.2433 | 6905.5 | 0.00 | 0.00 | None |
| 5.3923 | ...4255 | 0.0000 | 1995.02 | 8.12 | 0.2875 | 935.7 | 0.00 | 0.00 | None |
| 4.8126 | ...4201 | 0.0000 | 573.48 | 2.33 | 0.1969 | 184.2 | 0.00 | 0.00 | None |
| 4.6477 | ...0799 | 0.0000 | 608.96 | 2.48 | 0.1937 | 192.4 | 0.00 | 0.00 | None |
| 4.4194 | ...0753 | 0.0000 | 3097.61 | 12.60 | 0.2249 | 1136.2 | 0.00 | 0.00 | None |
| 4.3295 | ...4968 | 0.0000 | 2883.43 | 11.73 | 0.2003 | 961.9 | 0.00 | 0.00 | None |
| 4.0578 | ...8856 | 0.0000 | 596.59 | 2.43 | 0.2571 | 250.2 | 0.00 | 0.00 | None |
| 3.9571 | ...4492 | 0.0000 | 2672.08 | 10.87 | 0.2472 | 1089.2 | 0.00 | 0.00 | None |
| 3.8028 | ...3732 | 0.0000 | 2211.20 | 9.00 | 0.2046 | 880.2 | 0.00 | 0.00 | None |
| 3.6637 | ...2736 | 0.0000 | 2507.94 | 10.20 | 0.2096 | 857.4 | 0.00 | 0.00 | None |
| 3.5558 | ...0217 | 0.0000 | 1559.77 | 6.35 | 0.1163 | 347.5 | 0.00 | 0.00 | None |
| 3.4692 | ...6571 | 0.0000 | 317.79 | 1.29 | 0.1324 | 70.0 | 0.00 | 0.00 | None |
| 3.3832 | ...3211 | 0.0000 | 3880.39 | 15.79 | 0.2209 | 1398.3 | 0.00 | 0.00 | None |
| 3.3382 | ...6824 | 0.0000 | 3162.01 | 12.86 | 0.1957 | 1009.6 | 0.00 | 0.00 | None |
| 3.1691 | ...1343 | 0.0000 | 338.35 | 1.38 | 0.1826 | 100.8 | 0.00 | 0.00 | None |
| 3.0155 | ...5995 | 0.0000 | 1061.62 | 4.32 | 0.3053 | 528.7 | 0.00 | 0.00 | None |
| 2.8269 | ...6239 | 0.0000 | 1129.21 | 4.59 | 0.1882 | 529.1 | 0.00 | 0.00 | None |
| 2.7887 | ...0687 | 0.0000 | 463.97 | 1.89 | 0.1440 | 109.0 | 0.00 | 0.00 | None |
| 2.7081 | ...0497 | 0.0000 | 669.90 | 2.73 | 0.1461 | 172.0 | 0.00 | 0.00 | None |
| 2.6799 | ...4080 | 0.0000 | 353.53 | 1.44 | 0.1911 | 143.6 | 0.00 | 0.00 | None |
| 2.5206 | ...5871 | 0.0000 | 642.64 | 2.61 | 0.1066 | 113.2 | 0.00 | 0.00 | None |
| 2.3235 | ...7225 | 0.0000 | 920.57 | 3.74 | 0.2315 | 347.7 | 0.00 | 0.00 | None |

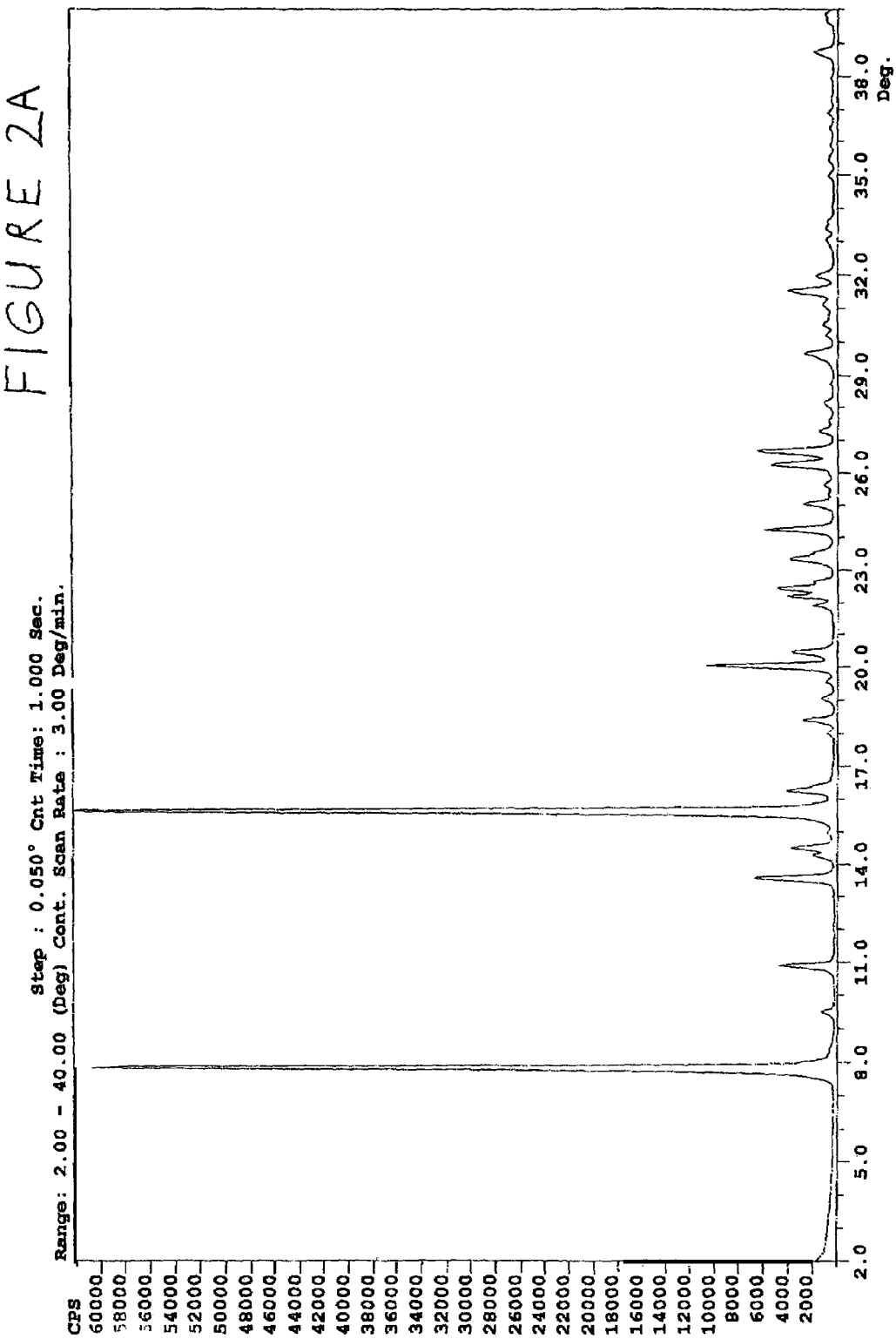

FIGURE 2B

:: D:\Thermo ARL\datafiles\samples\Mycophenol sav2\
s:

| Position (Deg.) | (DSp.) | Corr.Fact | Intensity (CPS) | Rel. Int. (%) | FWHM (Deg.) | (L) | Area (CPS.Deg.) | Strain Å | CSize Å | CSize source |
|---|---|---|---|---|---|---|---|---|---|---|
| 7.8111 | 11.3091 | 0.0000 | 45489.01 | 95.58 | 0.1139 | | 9232.1 | 0.00 | 0.00 | None |
| 9.4887 | 9.3130 | 0.0000 | 688.35 | 1.45 | 0.1338 | | 156.6 | 0.00 | 0.00 | None |
| 10.8842 | 8.1219 | 0.0000 | 3051.88 | 6.41 | 0.1543 | | 768.1 | 0.00 | 0.00 | None |
| 13.5522 | 6.5284 | 0.0000 | 4548.97 | 9.56 | 0.1614 | | 1197.9 | 0.00 | 0.00 | None |
| 14.2565 | 6.2074 | 0.0000 | 982.36 | 2.06 | 0.1431 | | 229.3 | 0.00 | 0.00 | None |
| 14.4925 | 6.1068 | 0.0000 | 2268.64 | 4.77 | 0.1452 | | 537.3 | 0.00 | 0.00 | None |
| 15.6119 | 5.6714 | 0.0000 | 47592.21 | 100.00 | 0.1271 | | 10604.6 | 0.00 | 0.00 | None |
| 16.2628 | 5.4458 | 0.0000 | 2522.14 | 5.30 | 0.1605 | | 725.7 | 0.00 | 0.00 | None |
| 17.9954 | 4.9252 | 0.0000 | 322.66 | 0.68 | 0.1000 | | 52.6 | 0.00 | 0.00 | None |
| 18.3940 | 4.8194 | 0.0000 | 1708.69 | 3.59 | 0.1396 | | 389.1 | 0.00 | 0.00 | None |
| 19.0493 | 4.6550 | 0.0000 | 631.58 | 1.33 | 0.1386 | | 142.8 | 0.00 | 0.00 | None |
| 19.4397 | 4.4272 | 0.0000 | 7317.31 | 15.38 | 0.1372 | | 1639.1 | 0.00 | 0.00 | None |
| 20.4576 | 4.3377 | 0.0000 | 2293.02 | 4.82 | 0.1728 | | 653.4 | 0.00 | 0.00 | None |
| 20.8990 | 4.0553 | 0.0000 | 1009.35 | 2.12 | 0.1000 | | 169.6 | 0.00 | 0.00 | None |
| 21.1699 | 4.0064 | 0.0000 | 2628.36 | 5.52 | 0.1000 | | 428.7 | 0.00 | 0.00 | None |
| 22.4159 | 3.9630 | 0.0000 | 3169.08 | 6.66 | 0.1607 | | 977.1 | 0.00 | 0.00 | None |
| 23.3226 | 3.8109 | 0.0000 | 2761.60 | 5.80 | 0.1456 | | 934.5 | 0.00 | 0.00 | None |
| 23.2384 | 3.6689 | 0.0000 | 4073.96 | 8.56 | 0.1289 | | 884.3 | 0.00 | 0.00 | None |
| 25.0334 | 3.5542 | 0.0000 | 1629.13 | 3.42 | 0.1450 | | 385.4 | 0.00 | 0.00 | None |
| 26.2441 | 3.3929 | 0.0000 | 3800.00 | 7.98 | 0.1502 | | 984.1 | 0.00 | 0.00 | None |
| 26.6497 | 3.3422 | 0.0000 | 4425.97 | 9.30 | 0.1632 | | 1178.3 | 0.00 | 0.00 | None |
| 28.1243 | 3.1702 | 0.0000 | 432.07 | 0.91 | 0.1682 | | 118.5 | 0.00 | 0.00 | None |
| 29.6143 | 3.0140 | 0.0000 | 1395.84 | 2.93 | 0.2263 | | 515.3 | 0.00 | 0.00 | None |
| 31.1169 | 2.8718 | 0.0000 | 469.53 | 0.99 | 0.1000 | | 103.4 | 0.00 | 0.00 | None |
| 31.5038 | 2.8374 | 0.0000 | 2511.14 | 5.28 | 0.1749 | | 716.2 | 0.00 | 0.00 | None |
| 31.9728 | 2.7969 | 0.0000 | 977.36 | 2.05 | 0.1462 | | 233.1 | 0.00 | 0.00 | None |
| 33.0269 | 2.7100 | 0.0000 | 210.54 | 0.44 | 0.2191 | | 75.3 | 0.00 | 0.00 | None |
| 33.4036 | 2.6803 | 0.0000 | 366.25 | 0.77 | 0.1000 | | 130.5 | 0.00 | 0.00 | None |
| 38.6945 | 2.3251 | 0.0000 | 1110.81 | 2.33 | 0.1917 | | 312.6 | 0.00 | 0.00 | None |

PROCESS FOR PREPARATION OF MYCOPHENOLIC ACID AND ESTER DERIVATIVES THEREOF

CROSS-REFERENCE TO RELATED APPLICATIONS

This application claims the benefits of U.S. Provisional Patent Application Nos. 60/565,694, filed Apr. 26, 2004 and 60/572,527, filed May 18, 2004, the contents of all of which are incorporated herein by reference.

FIELD OF THE INVENTION

The invention relates to isolation of mycophenolic acid.

BACKGROUND OF THE INVENTION

Mycophenolic acid, has the chemical name 6-[4-Hydroxy-6-methoxy-7-methyl-3-oxo-5-phthalanyl]-4-methyl-4-hexenoic acid, 6-[1,3-Dihydro-4-hydroxy-6-methoxy-7-methyl-3-oxo-5-isobenzofuranyl]-4-methyl-4-hexenoic acid, molecular formula of $C_{17}H_{20}O_6$, molecular weight of 320.35, CAS Registry number of 24280-93-1 and a structure of:

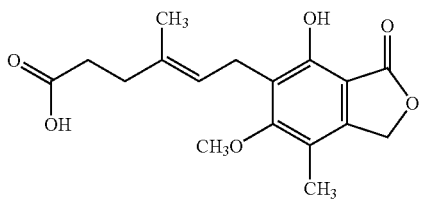

Mycophenolic acid (MPA), isolated by Gosio in 1893, is the first well characterized antibiotic (Bentley 2001). It is produced by several species of Penicillium, including P. brevi-compactum, P. scabrum, P. nagemi, P. roqueforti, P. patris-mei and P. viridicatum (Clutterbuck et al. 1932, Jens and Filtenborg 1983).

MPA, in addition to its antibiotic activity (Abraham 1945), also has antifungal (Gilliver 1946), antiviral (Ando et al. 1968) and antitumor properties (Noto et al. 1969), and has been used clinically in the treatment of psoriasis (Johnson 1972). More recently, it has been recognized as a powerful immunosuppressant (Bentley 2000).

At least one reason for the pharmacological properties of MPA is that in several biological systems it interferes with guanine biosynthesis at the level of inosine monophosphate dehydrogenase (IMPD). MPA has, therefore, a pronounced inhibitory effect on nucleic acid synthesis (Franklin and Cook 1969). The inhibition of IMPD is also the basis for the lymphocyte-specific immunosuppressive effect of MPA. Since lymphocytes primarily depend on de novo guanine biosynthesis, the reduction of this pathway results in suppression of T and B lymphocyte proliferation.

MPA was withdrawn due to its high incidence of side effects (primarily infections such as herpes zoster and gastrointestinal side effects such as stomach discomfort). The 2-morpholinoethyl ester derivative, mycophenolate mofetil (CellCept®) does not have these drawbacks and has a better bioavailability than mycophenolic acid. Mycophenolate mofetil was recently approved (in the United States in 1995 and in Europe in 1996) for prophylaxis of organ rejection in patients receiving allogeneic renal transplants (Shaw and Nowak 1995, Sollinger 1995). After oral administration, the ester form rapidly hydrolyzes to free acid. MPA is then converted mainly to an inactive glucuronide metabolite, which is eliminated by urinary excretion (Bentley 2001, Wiwattanawongsa et al. 2001).

MPA is isolated from a fermentation broth in WO 01/21607, WO 01/64931 and GB 1158387. The isolation of MPA from a fermentation broth however is inefficient. The MPA isolated by conventional processes has a high degree of impurities.

The invention provides an efficient process for isolation of mycophenolic acid.

SUMMARY OF THE INVENTION

The invention is directed towards mycophenolic acid and esters thereof.

One embodiment of the invention is directed towards processes for isolating mycophenolic acid comprising providing a concentrated alkaline mixture containing mycophenolic acid; admixing the mixture with a first water-immiscible solvent to form an aqueous phase and a first water-immiscible phase; separating the aqueous phase; admixing the aqueous phase with a second water-immiscible solvent at a pH of less than about 7 to form an aqueous phase and a second water-immiscible phase; separating the second water-immiscible phase; concentrating the second water-immiscible phase; and crystallizing mycophenolic acid.

Preferably, the concentrated alkaline mixture containing mycophenolic acid is prepared by a process comprising the steps of basifying a fermentation broth containing mycophenolic acid and removing the mycelia to obtain a basic mixture; acidifying the basic mixture to obtain an acidic mixture; and filtering and basifying the acidic mixture to obtain the concentrated alkaline mixture.

The concentrated alkaline mixture containing mycophenolic acid may also be prepared by whole broth extraction.

Preferably, the concentrated alkaline mixture and the first water-immiscible solvent are admixed at a pH of about 8 to about 11. The pH is preferably adjusted with ammonium hydroxide or sodium hydroxide.

Preferably, at least one of the first or second water-immiscible solvent is a $C_4$ to $C_7$ ester, a $C_4$ to $C_7$ ketone, or mixtures there. More preferably, at least one of the first or second water-immiscible solvent is ethylacetate, isobutylacetate, n-butylacetate, or mixtures thereof. Ethylacetate is most preferred.

The aqueous phase formed after admixing the concentrated alkaline mixture with the first water-immiscible phase is preferably further extracted at least once prior to admixing with the second water-immiscible solvent.

Preferably, the aqueous phase and the second water-immiscible solvent are admixed at a pH of about 5 to about 6.5. The pH is preferably adjusted with at least one of sulfuric acid, phosphoric acid, or hydrochloric acid.

The aqueous phase formed after admixing with the second water-immiscible solvent is preferably further extracted at least once.

The resulting water-immiscible phase from the extraction is preferably concentrated by distillation prior to crystallization, more preferably by filtration, and most preferably by membrane filtration. A preferred filtration membrane is plastic filtration membrane.

Crystallization of mycophenolic acid is preferably carried out by cooling the concentrate.

In a preferred embodiment, the mycophenolic acid isolated by the processes of the invention has a purity of at least about 99.5% as measured by HPLC area percentage.

The invention also encompasses processes for preparing a concentrated alkaline mixture containing mycophenolic acid comprising basifying a fermentation broth containing mycophenolic acid and removing mycelia to obtain a basic mixture; acidifying the basic mixture to obtain an acidic mixture; and filtering the acidic mixture at an alkaline pH to obtain the concentrated alkaline mixture.

Filtration is preferably carried out using membrane filtration. The preferred filtration membrane is ceramic membrane or plastic microfiltration membrane.

Preferably, the mycelia is removed by filtration. Preferred methods for removing mycelia include microfiltration membrane, vacuum filter, belt filter, press filter, nuts filter, centrifuge, or solid bowl centrifuge.

The invention further encompasses processes for preparing mycophenolic acid ester comprising providing a concentrated alkaline mixture containing mycophenolic acid; admixing the mixture with a first water-immiscible solvent to form an aqueous phase and a first water-immiscible phase; separating the aqueous phase; admixing the aqueous phase with a second water-immiscible solvent at a pH of less than about 7 to form an aqueous phase and a second water-immiscible phase; separating the second water-immiscible phase; concentrating the second water-immiscible phase; crystallizing mycophenolic acid; and converting the mycophenolic acid to an ester.

Preferably, the ester is morpholinoethyl ester. Also preferably, the ester is a $C_1$ to $C_4$ alkyl ester, and more preferably a methyl ester or t-butyl ester.

In one embodiment, the invention encompasses mycophenolic acid in solid state having a purity of at least about 99.5%, and preferably at least about 99.9%, as measured by HPLC area percentage.

The invention also encompasses mycophenolic acid in solid state having a of total impurity content of less than about 0.1%, and preferably less than about 0.08%, as measured by HPLC area percentage.

The invention further encompasses mycophenolic acid in solid state having a melting point of about 141.6° C. to about 144.6° C., and more preferably a melting point of about 143.1° C.

In another embodiment, the invention encompasses a pharmaceutical composition comprising the mycophenolic acid of the invention or an ester thereof, and a pharmaceutically-acceptable excipient. The preferred ester is morpholinoethyl ester.

The invention also encompasses a method of suppressing an immune system of a mammal in need thereof by administering a therapeutically effective amount of the composition of the invention to the mammal.

BRIEF DESCRIPTION OF THE FIGURES

FIG. 1A is a powder XRD pattern of a sample of mycophenolic acid produced by Example 9.

FIG. 1B is a table of powder XRD values corresponding to FIG. 1A.

FIG. 2A is a powder XRD pattern of a sample of mycophenolic acid produced by Example 10.

FIG. 2B is a table of powder XRD values corresponding to FIG. 2A.

DETAILED DESCRIPTION OF THE INVENTION

The present invention encompasses processes for isolating mycophenolic acid. The isolation process of the invention may produce MPA having less than about 0.1% of each impurity. More specifically, the invention encompasses a process for purifying mycophenolic acid from a concentrated alkaline mixture of the acid. Also provided are processes for preparing the concentrated alkaline mixture containing the acid from a fermentation broth.

As used herein, the term "mixture" includes both heterogeneous and homogenous mixtures, such as, for example, a solution, suspension, or slurry. A heterogeneous mixture may be formed, for example, during extraction, where mycophenolic acid is dissolved in a solvent by basification. Since the heterogeneous mixture may also contain other impurities, a clear solution might not result without filtration.

As used herein, the term "alkaline" or "basic" refers to a pH of greater than about 7.

As used herein, the term "acidic" refers to a pH of less than about 7.

The pH values referred to throughout the application refer to the pH of aqueous phases.

As used herein, the term "concentrated" in reference to the mixture of mycophenolic acid prior to isolation means a concentration of about 5 g/l or greater of mycophenolic acid. Calculating from the volume of the fermentation broth, approximately ⅓ volume or less of concentrated solution or heterogeneous mixture is obtained from 1 volume of the fermentation broth.

Fermentation processes commonly known in the art may be used to obtain MPA from the penicillium strain, such as illustrated in GB 1,157,099 or JP 59091891 to obtain a fermentation broth.

The concentrated mixture may be prepared from a fermentation broth by various methods, such as whole broth extraction, where the extract of an entire fermentation broth is concentrated into a residue.

In another embodiment, the present invention provides a process for obtaining a concentrated alkaline mixture of mycophenolic acid. The fermentation broth is initially basified, followed by removal of the mycelia by filtration to obtain a filtrate. Subsequent acidification of the filtrate leads to solidification of MPA. In this step, crystals or a suspension is formed. Concentration of the MPA is achieved using any filter known to the skilled artisan, such as vacuum drum filter, microfiltration membrane, a belt filter, a press filter, a nuts filter, a centrifuge, or a solid bowl centrifuge. Following filtration, the solid or suspension obtained may be added to an aqueous solvent, preferably water, and then basified to obtain an aqueous alkaline solution of MPA.

Preferably, the fermentation broth is initially basified to a pH of at least about 8, and more preferably at a pH of about 8 to about 11.

Preferably, the filtrate is acidified to a pH of less than about 6, and more preferably at a pH of about 4 to about 5.5.

Common filtration methods known in the art may be used for filtration of the fermentation broth or during other stages of the process. In one embodiment, filtration is carried out by using a microfiltration membrane such as, for example, a ceramic membrane or a plastic microfiltration membrane. Preferably, the microfiltration membrane contains membrane channels or membrane tubes. The microfiltration membrane technology is an economical method to obtain concentrated mycophenolic acid solution or suspension.

Any suitable ceramic microfiltration membrane, such as those illustrated in Example 4, may be used. Ceramic membranes may be obtained from companies such as Atech Innovations Gmbh (Gladbeck, Germany), US Filter (Sturbridge, Mass.), CeraMem Corporation (Waltham, Mass.), or PALL (East Hills, N.Y.). Any pore size suitable for microfiltration may be used. Preferably, the pore size is in a range of about 50 nm to about 5000 nm, and more preferably about 100 nm to about 250 nm. The ceramic membrane may be made of materials such as, for example, alfa-alumina, silica, or silicon carbide. Generally, the membrane is tubular, though the cross-section can also be quadratic.

In another embodiment, plastic microfiltration membranes are used. Any suitable plastic microfiltration membrane, such as those illustrated in Examples 5 and 6, may be used. The pore size, membrane material, or shape may vary depending on the type of plastic microfiltration membrane used. For example, Membrane MFK-617 made by KOCH (Wilmington, Mass.) has a pore size of less than about 500 nm. Membrane MFK-617 is tubular, and is made of PES. Membrane HFM-180 made by KOCH has a cut-off of about 250,000 D, which is equal to approximately 100 nm to 250 nm in pore size. HFM-180 is tubular, and is made from PVDF.

Hollow fiber type membranes are also suitable, e.g., PM-100 or PM-500, both produced by KOCH. Both membranes are made of PS. The molecular weight cut-off for PM-100 is 100,000 D. The cut-off for PM-500 is 500,000 D.

After the concentrated alkaline mixture is prepared, by the process described above or by whole broth extraction, the present invention provides an efficient process for isolating mycophenolic acid from the mixture.

MPA may be isolated by extraction of an aqueous concentrated alkaline mixture with a water-immiscible solvent. In one embodiment, MPA is isolated by a first extraction of the concentrated mixture with a water-immiscible solvent, preferably at a basic pH, to remove impurities in the alkaline solution, followed by a second extraction, preferably at an acidic pH, to obtain a solution of MPA in the organic solvent.

In one embodiment, MPA is isolated by admixing an aqueous concentrated alkaline mixture with a water-immiscible solvent to form an aqueous phase, separating the aqueous phase, admixing the aqueous phase with a water-immiscible solvent at a pH of less than about 7 to form an aqueous phase and a water-immiscible phase, separating the water-immiscible phase, concentrating the water-immiscible phase, and crystallizing mycophenolic acid from the concentrate.

Impurities may be removed from the first extraction of the alkaline solution or mixture with the water-immiscible organic solvent. Preferably, the first extraction is at a basic pH, preferably at a pH of at least about 8, and more preferably at about 8.3 to about 9.2. This extraction step is preferably carried out at least twice.

After the first extraction, the aqueous phase may be acidified to a pH of less than about 7, preferably about 5 to about 6.5 for a second extraction with a water-immiscible organic solvent to obtain a solution of mycophenolic acid in the organic solvent. The second extraction may also be repeated. Preferably, the extracted organic phases are combined.

The processes of the invention for isolating mycophenolic acid provide efficient removal of MPA impurities and related substances. By implementing a series of alkaline and acidic extractions, the MPA is obtained more easily, and at a high level of purity.

Mycophenolic acid may be recovered from the solution by crystallization. Prior to crystallization, the solution may be concentrated. For example, the solution may be concentrated by evaporation. Evaporation may be carried out under ambient or reduced pressure, or optionally by heating, such as at reflux temperature. The solution may also be concentrated by membrane filtration. Preferably, the solution is concentrated by distillation at atmospheric pressure or under reduced pressure. The term "reduced pressure" refers to a pressure below one atmosphere, preferably below about 100 mmHg. Preferably, the solution is concentrated to about 100 g/l to about 300 g/l, and more preferably to about 200 g/l.

Crystallization of mycophenolic acid from the solution is preferably carried out by cooling. Preferably, crystallization from solvents such as ethyl acetate is done by cooling the solution to a temperature of about 0° C. to about −20° C., and more preferably to about −10° C. Other suitable solvents for crystallization include, but are not limited to, isobutylacetate, acetone, isopropanol, water (at higher temperature), toluene/acetone mixture, ethanol/water mixture or methanol/water mixture, generally $C_3$ to $C_7$ esters or $C_3$ to $C_7$ ketones, or $C_1$ to $C_4$ alcohols. The solvent may be heated at a suitable temperature to dissolve the mycophenolic acid before crystallization. For example, where water is used as a crystallization solvent, the water may be heated at a temperature of at least about 50° C.

The recovered crystals may be dried, preferably at a temperature of about 50° C. to about 70° C. Preferably, the crystals are dried under reduced pressure, i.e., less than 1 atmosphere, and more preferably under a pressure of less than about 100 mm Hg. Optionally, the crystals may be recrystallized. The recrystallization may optionally be carried out after first treating with charcoal.

A basic pH may be obtained preferably with ammonium hydroxide or other suitable bases. Examples of bases include, for example, an organic amine, an alkali metal hydroxide, an alkaline earth metal hydroxide, or an alkali or alkaline earth metal carbonate or hydrogen carbonate salt. Specific examples of bases include, for example, 1,8-bis(N,N-dimethylamino)napthalene, tri-ethyl amine, sodium methoxide, sodium hydroxide, potassium hydroxide, calcium hydroxide, magnesium hydroxide, sodium carbonate, potassium carbonate, sodium hydrogencarbonate, potassium hydrogencarbonate, calcium carbonate or basic alumina. A preferred base is ammonium hydroxide.

An acidic pH may be obtained using acids suitable for adjusting the pH of a solution, such as, for example, sulfuric acid, phosphoric acid or hydrochloric acid. Preferred acids include sulfuric acid or phosphoric acid.

The water-immiscible organic solvent may be independently selected at each stage of extraction. Any water-immiscible solvent suitable for extraction of MPA may be used. Examples of suitable solvents include, but are not limited to, at least one of a $C_4$ to $C_7$ ester or ketone. More particularly, suitable esters have the general formula $R_1$—C(O)O—$R_2$, wherein $R_1$ is H or linear or branched C1-6 alkyl, and $R_2$ is linear or branched C1-6 alkyl. Examples of suitable esters include, but are not limited to, methyl acetate, ethyl acetate, n-propyl acetate, iso-propyl acetate, n-butyl acetate, iso-butyl acetate, t-butyl acetate, methyl formate, n-propyl formate, iso-propyl formate, n-butyl formate, or iso-butyl formate. More particularly, suitable aliphatic ketones have the general formula $R_1$—C(O)—$R_2$, wherein $R_1$ and $R_2$ are, independently, linear or branched alkyl groups, each having from 1 to 4 carbon atoms. Examples of aliphatic ketones include, but are not limited to methyl ethyl ketone or methyl iso-butyl ketone. Additionally, solvents such as dichloromethane or dichloroethane may also be used.

The mycophenolic acid of the present invention has an assay of 100%. An assay refers to a determination of purity or presence of a quantity of a substance, as described by the European Pharmacopoeia ("EP"). *European Pharmacopoeia,* 4th Ed, Council of Europe, Strasbourg, 2001. The assay is performed with high pressure liquid chromatography ("HPLC").

In one embodiment, the present invention provides MPA having a melting point of about 141.6° C. to about 144.6° C., and more preferably about 143.1° C.

In another embodiment, the present invention provides MPA having a purity of about at least about 99.5%, and more preferably at least about 99.9%. Preferably, the MPA has a total impurity content of less than about 0.2%, and more preferably less than 0.08% as measured by area percentage HPLC.

The mycophenolic acid prepared herein may be converted to a an ester, such as a $C_1$ to $C_4$ alkyl ester such as methyl, ethyl or t-butyl ester. A preferred embodiment is a morpholinoethyl ester of the acid. Esterification of mycophenolic acid may be carried out by methods known in the art. See, e.g., U.S. Pat. Nos. 4,753,935, 5,543,408 and 5,247,083, WO 00/34503, and WO 02/100855.

Pharmaceutical formulations of the present invention contain mycophenolic acid or an ester or salt thereof. The invention also encompasses a method of suppressing the immune system of a mammal by administering a therapeutically effective amount of the pharmaceutical composition to a mammal in need thereof.

The pharmaceutical composition may contain only a single polymorphic form, or a mixture of various crystalline forms, with or without amorphous form. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, MPA and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration.

Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

EXAMPLES

Analytical HPLC Method

HPLC analysis was conducted using a Discovery ciano or Zorbax $C_8$ column. The eluent was a water-acetonitrile mixture containing phosphoric acid and the potassium salt of phosphoric acid. The triethylamine salt of phosphoric acid may be used in place of the potassium salt of phosphoric acid. The pH of the eluent was 3.0-5.9. The eluent flow was approximately 1.5 ml/min. The temperature for elution was 20-45° C.

Example 1

Purification of Mycophenolic Acid

A concentrated mycophenolic acid suspension of 140 kg (produced from 620 kg fermented broth) was adjusted with 800 ml conc. ammonium hydroxide solution to a pH of 8.3-8.5. The alkaline solution was purified with 80 liters of ethylacetate. The ethylacetate was mixed to the alkaline solution, stirred for 30 minutes, and the phases were separated.

To the obtained (147 kg) aqueous phase, 80 liters of ethylacetate was added. The pH was adjusted to 5.8 with sulfuric acid, stirred for 30 minutes, and the phases were separated.

To the obtained (150 kg) aqueous phase, 40 liters of ethylacetate was added. The pH was adjusted to 5.9, stirred for 30 minutes, and phases were separated.

The ethylacetate phases of the two acidic extractions were combined and concentrated to approx. 200 g/l concentration at max. 70° C. under reduced pressure. Concentrated ethylacetate solution was heated to 60-65° C., cooled to −10° C. at a cooling rate of approx. 3° C./hour, and allowed to crystallize for 18 hours at −10° C. The crystals were filtered and coverwashed with cooled ethylacetate. The crystals were dried at max. 70° C. under reduced pressure. Mass of crystals: 1250 g. Assay: 99.0%.

The crystals were recrystallized from ethylacetate after treatment with charcoal. Assay of recrystallized product is 99.6%. HPLC purity of the crystals is 99.8%. Any impurity is less than 0.1%.

Example 2

Purification of Mycophenolic Acid

To 119.4 kg concentrated mycophenolic acid suspension (produced from 420 kg fermented broth), 71.6 liters of ethylacetate was added. The pH was adjusted to 9.1 with conc. ammonia solution, stirred for 30 minutes, and the phases were separated.

To the (126.8 kg) aqueous phase, 63.4 liters of ethylacetate was added. The pH was adjusted to 9.1-9.2 with conc. ammonia solution, stirred for 30 minutes, and the phases were separated.

To the obtained (129.5 kg) aqueous phase, 71.6 liters of ethylacetate was added. The pH was adjusted to 5.6-5.7 with sulfuric acid, stirred for 30 minutes, and the phases were separated.

To the obtained (130.6 kg) aqueous phase, 39.2 liters of ethylacetate was added. The pH was adjusted to 5.9 with conc. ammonia solution, stirred for 30 minutes, and the phases were separated.

The ethylacetate phases of the two acidic extractions were combined and concentrated to approx. 200 g/l concentration at max. 70° C. under reduced pressure.

The concentrated ethylacetate solution was heated to 60-65° C., cooled to −10° C. at a cooling rate of approx. 3° C./hour, and allowed to crystallize for 3 hours at −10° C. The crystals were filtered and coverwashed with cooled ethylacetate. The crystals were dried at max. 70° C. under reduced pressure. Mass of crystals: 553 g. Assay: 98.2%.

The crystals were recrystallized from ethylacetate after treatment with charcoal. Assay of recrystallized product is 99.2%. HPLC purity of the crystals is 99.7%. Any impurity is less than 0.1%.

Example 3

Preparation of Concentrated Mycophenolic Acid

Fermented broth (15 kg) was adjusted to pH 8.0-11.0. The alkaline fermented broth was filtered, and the filtered mycelia was washed with water. The filtrate was 37.6 kg. 91.1% of the fermented active substance was obtained in the filtrate. The pH of the filtrate was adjusted to pH 2.0-2.2 with sulfuric acid. Filtration aid (perlite) was added to the acidic filtrate, and the precipitate was filtered. The filtered precipitate was suspended in 5 liters of water, and the pH of the suspension was adjusted to pH 8.0-11.0 with sodium hydroxide solution. The alkaline suspension was filtered and washed to obtain an alkaline filtrate of 8 liters.

This alkaline suspension is used for purification of mycophenolic acid, such as in Examples 1 or 2.

Example 4

Preparation of Concentrated Mycophenolic Acid

Fermented broth (45 kg) was adjusted to pH 8.0-11.0. The alkaline fermented broth was filtered, and the filtered mycelia was washed with water. The filtrate was 113.7 kg. 93.2% of the fermented active substance was obtained in the filtrate. The pH of the filtrate was adjusted to pH 4.0-4.5 with diluted phosphoric acid. The suspension was filtered by microfiltration ceramic membrane of 100 nm to 250 nm pore size. The concentrated suspension (approx. 10 liters) was adjusted to pH 7.5-11.0 with ammonium hydroxide solution.

This alkaline suspension is used for purification of mycophenolic acid, such as in Examples 1 or 2.

Example 5

Preparation of Concentrated Mycophenolic Acid

Fermented broth (220 kg) was adjusted to approx. pH 8.0. The fermented broth was filtered by microfiltration plastic membranes (e.g. MFK-617 and HFM-180, by KOCH). Water was added continuously for dilution during filtration. 1100 kg of filtrate was obtained. The filtered broth was adjusted to approx. pH 4.0, and the crystal suspension was concentrated to approx. 70 liters. The pH of the concentrated acidic suspension was then adjusted to an alkaline pH of 7.5-11.0.

This alkaline suspension is used for purification of mycophenolic acid, such as in Examples 1 or 2.

Example 6

Purification of Mycophenolic Acid

To 14 m$^3$ of harvested fermented broth, the same volume of drinking water was added, followed by 168 liters (1.2%) of conc. ammonia solution. Filter aid (perlite) in 1% mass of the starting fermented broth was added, and the pH was adjusted to between 8.0-8.5 by adding conc. 85% phosphoric acid solution (approx. 100 liters). The treated broth was kept at ambient temperature without stirring for at least 6 hours. Filtration was carried out on vacuum drum filter during coverwashing with drinking water. Filtrate of 42 m$^3$ was collected. Yield from filtration of the fermented broth was approx. 90%.

The pH of the filtered fermented broth was adjusted to 4.0-4.5 by adding 20% sulfuric acid solution (approx. 300 liters). After at least 3 hours, the precipitated crude crystals were filtered and concentrated on microfiltration membrane (MFK-617, by KOCH). The pH-adjusted 42 m$^3$ filtered fermented broth was concentrated to ¹/₄₀ volume (approx. 1.0-1.2 m$^3$). The filtration time was approx. 60 hours. The concentrated solution was diluted with approx. 2 m$^3$ acidic water, and the solution was concentrated again to 1.0-1.2 m$^3$. After removing the concentrated solution, the equipment was washed with 0.3-0.5 m$^3$ of acidic drinking water. Yield from precipitation and concentration is approx. 80%.

The 1.0-1.2 m$^3$ concentrate and the 0.3-0.5 m$^3$ acidic washing water were combined, 0.5-0.6 folds volume of ethylacetate was added (approx. 0.8 m$^3$), and the pH was adjusted to between 9.0-9.2 with conc. ammonia solution. Extraction was carried out for 30 minutes, and the pH was adjusted to between 9.0-9.2. The phases were then separated.

To the aqueous phase, 0.5-0.6 folds volume of ethylacetate was added (approx. 0.8 m$^3$) again (calculated to the volume of the combined acidic concentrate), and the pH was adjusted to between 9.0-9.2 with conc. ammonia solution/20% sulfuric acid solution. Extraction was carried out for 30 minutes, and the pH was adjusted to between 9.0-9.2. The phases were then separated.

To the aqueous phase, 0.5-0.6 folds volume of ethylacetate was added (calculated to the volume of the combined acidic concentrate), and the pH was adjusted to 5.8-6.1 with 20% sulfuric acid solution. Extraction was carried out for 30 minutes, and the pH was adjusted to between 5.8-6.1. The phases were then separated.

To the aqueous phase, 0.25-0.3 folds volume of ethylacetate was added (calculated to the volume of the combined acidic concentrate), and the pH was adjusted to 6.3-6.5 with conc. ammonia solution. Extraction was carried out for 30 minutes, and the pH was adjusted to between 6.3-6.5. The phases were then separated.

The third and fourth ethylacetate phases were combined and evaporated to approx. 200 g/l (based on evaporation residue of the combined phases) at max 70° C. under reduced pressure. The final volume of the evaporation was approx. 150 liters. Yield from extraction and evaporation was approx. 90%.

The ethylacetate concentrate (approx. 150 liters) was cooled to −10° C. to −17° C. (cooling rate approx. 3° C./hour), and crystallized at this temperature for at least 2 hours. The crystals were washed with 45 liters of chilled ethylacetate and dried at max. 70° C. under reduced pressure. Mass of the crystals was approx. 25 kg. Yield from crystallization was approx. 87%.

The crystals (25 kg) were dissolved in 10 times mass:volume (250 liters) of ethylacetate at 60-65° C. The solution was treated with charcoal and then filtered. Mycophenolic acid was crystallized at −10° C. to −17° C., and the crystals were filtered and coverwashed with 75 liters of ethylacetate at −10° C. to −17° C. The crystals were dried at max. 70° C. under reduced pressure. Yield from final crystallization was approx. 90%.

Example 7

Purification of Mycophenolic Acid

Fermented broth was filtered in 3 parts (3×225 kg).

To the first 225 kg fermented broth, the same volume of water was added, followed by 1.2% conc. ammonia solution (calculated to the mass of the fermented broth), and the pH was adjusted to 8.0-8.5 by adding 20% phosphoric acid solution. The treated broth was kept without stirring for approx. 6 hours and filtered by microfiltration plastic membranes (MFK-617 and HFM-180, by KOCH) at 40-43° C. Water was added continuously for dilution during the filtration. 1125 kg of filtrate was obtained.

The pH of the filtrate was adjusted to 4.0-4.5 by adding 20% sulfuric acid. After approx. 3 hours, the crystal suspension was concentrated to approx. 70 liters volume. The concentrated mycophenolic acid crystal suspension (approx. 70 liters) was collected, and the microfilters were washed with 70 liters of water by circulating the water. The washing (approx. 70 liters) was also collected.

The permeate of the acidic concentration was pH-adjusted to 8.0-8.5 by adding conc. ammonia solution and used for the dilution and filtration of the next 225 kg fermented broth.

The second (225 kg) and the third (225 kg) fermented broth filtration and acidic precipitate concentration was carried out in the same manner described above, except after the concentration of the third acidic precipitate (of 4.0-4.5), approx. 70 liters of the first and 70 liters of the second concentration were combined, and the total amount was concentrated to 100 kg. The crystal suspension was collected and washed with 70 liters of water to obtain 74 liters of washing. The concentrate and the washing were combined.

To 174 kg concentrated mycophenolic acid suspension (produced from 675 kg fermented broth), 104.4 liters of ethylacetate was added, and the pH was adjusted to 9.1 with conc. ammonia solution. Stirring was applied for 30 minutes, and the phases were separated. To the aqueous phase (183 kg), 104.4 liters of ethylacetate was added. The pH was adjusted to 9.2 with conc. ammonia solution, stirring was applied for 30 minutes, and the phases were separated.

To the obtained aqueous phase (185.4 kg), 104.4 liters of ethylacetate was added, and the pH was adjusted to 5.9-6.0 with sulfuric acid. Stirring was applied for 30 minutes, and the phases were separated. To the obtained aqueous phase (176.4 kg), 43.5 liters of ethylacetate was added. The pH was adjusted to 6.4 with conc. ammonia solution, stirring was applied for 30 minutes, and the phases were separated. The ethylacetate phases of the two acidic extractions were combined and concentrated to approx. 200 g/l concentration at max. 70° C. under reduced pressure. Concentrated ethylacetate solution was heated to 60-65° C., cooled to −10° C. at a cooling rate of approx 3° C./hour, and crystallized for 8 hours at −10° C. The crystals were filtered, coverwashed with cooled ethylacetate, and dried at max. 70° C. under reduced pressure. Mass of crystals: 970 g. Assay: 99.4%.

The crystals were recrystallized from ethylacetate after treatment with charcoal. HPLC purity of the crystals is 99.8%. Any impurity is less than 0.1%.

Example 8

Purification of Mycophenolic Acid

Mycophenolic acid is purified in a similar manner as Example 7, except the mycophenolic acid is purified at pH 9.0-9.2 three times.

Assay of final crystals is 100.0%. Total impurity content is 0.07%.

Example 9

Mycophenolic Acid

The melting point of the final product from Example 8 was 143.1° C.

The X-ray powder diffraction pattern is illustrated in FIG. 1.

Example 10

Mycophenolic Acid

Example 8 was repeated. The melting point of the final product was 143.1° C.

The X-ray powder diffraction pattern is illustrated in FIG. 2.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated by reference in their entirety.

REFERENCES

Abraham, E. P. 1945. The effect of mycophenolic acid on the growth of *Staphylococcus aureus* in heart broth. Biochem. J. 39:398-408.

Ando, K., Suzuki, S., Tamura, G. and Auma, K. 1968. Antiviral activity of mycophenolic acid. J. Antibiot. 21: 649-652.

Bedford, C. T., Knittel, P., Money, G. T., Phillips, G. T. and Salisbury, P. 1973. Biosynthesis of mycophenolic acid. Can. J. Chem. 51:694-697.

Bentley, R. 2000. Mycophenolic acid: a one hundred year odyssey from antibiotic to immunosuppressant. Chem. Rev. 100:3801-3825.

Bentley, R. 2001. Bartolomeo Gosio. Adv. Appl. Microbiol. 48:229-250.

Canonica, L., Kroszczynski, W., Ranzi, B. M., Rindone, B., Santaniello, E. and Scolastico, C. 1972. Biosynthesis of mycophenolic acid. J. Chem. Soc. Perkin I 21: 2639-2643.

Clutterbuck, P. W., Oxford, A. E., Raistrick, H. and Smith, G. 1932. CLXXI. Studies in the biochemistry of microorganisms. XXIV. The metabolic products of the *Penicillium brevi-compactum* series. Biochem. J. 26:1442-1458.

Detroy, R. W., Freer, S. N. and Fennel, D. I. 1973. Relationship between the biosynthesis of virus-like particles and mycophenolic acid in *Penicillium stoloniferum* and *P. brevi-compactum*. Can. J. Microbiol. 19:1459-1462.

Franklin, T. J. and Cook, J. M. 1969 The inhibition of nucleic acid synthesis by mycophenolic acid. Biochem. J. 113: 515-524.

Frisvad, J. C. and Filtenborg, O. 1983. Classification of terverticillate *Penicillia* based on profiles of mycotoxins and other secondary metabolites. Appl. Environ. Microbiol. 46:1301-1310.

Gainer, F. E. and Wesselman, H. J: 1970. GLC of mycophenolic acid and related compounds. J. Pharm. Sci. 59:1157-1159.

Gilliver, K. 1946. The inhibitory action of antibiotics on plant pathogenic bacteria and fungi. Ann. Bot. (London) 10: 271-282.

Johnson, I. S. 1972. Pharmaceuticals containing mycophenolic acid for treatment of psoriasis. Chem. Abstr. 77:928-53

Muth, W. L. and Nash, H. 1975. Biosynthesis of mycophenolic acid: Purification and characterization of S-adenosyl-L-methionine:demethylmycophenolic acid O-methyltransferase. Antimicrob. Agents Chemother. 8:321-327.

Neely, F. L. and Parks, R. J. 1991. High-performance liquid chromatographic determination of mycophenolic acid in fermentation broth. J. Chromatogr. 540:383-385.

Noto, T., Harada, Y. and Koyama, K. 1970. A turbidimetric bioassay method for determination of mycophenolic acid. J. Antibiot. 23: 96.

Noto, T., Sawada, M., Ando, K. and Kogama, K. 1969. Some biological properties of mycophenolic acid. J. Antibiot. 22:165-169.

Nulton, C. P. and Campbell, I. M. 1978. Labelled acetone and levulinic acid are formed when [14C]acetate is being converted to mycophenolic acid in *Penicillium brevicompactum*. Can. J. Microbiol. 24:199-201.

Ozaki, H., Ishihara, M., Kida, T., Yamakana, S. and Shibai, H. 1987. Mycophenolic acid production by drug-resistant and methionine or glutamic-acid requiring mutants of *Penicillium brevicompactum*. Agric. Biol. Chem. 51:2509-2514.

Pastore, A., Russo, A. L., Piemonte, F., Mannucci, L. and Federici, G. 2002. Rapid determination of mycophenolic acid in plasma by reversed-phase high-performance liquid chromatography. J. Chromatogr. 776:251-254.

Sadhukhan, A. K., Murthy, M. V. R., Kumar, R. A., Mohan, E. V. S., Vandana, G., Bhar, C. and Venkateswara Rao, K. 1999. Optimization of mycophenolic acid production in solid state fermentation using response surface methodology. JIMB. 22:33-38.

Shaw, L. M. and Nowak, I. 1995. Mycophenolic acid: measurement and relationship to pharmacologic effects. Therap. Drug Monit. 17:690-699.

Sollinger, H. W. 1995. Mycophenolate mofetil for the prevention of acute rejection in primary cadaveric renal allograft recipients. Transplantation: 60:225-232.

Wiwattanawongsa, K., Heinzen, E., Kemp, D. C., Dupuis, R. D. and Smith, P. C. 2001. Determination of mycophenolic acid and its phenol glucuronide metabolite in human plasma and urine by high-performance liquid chromatography. J. Chromatogr. B. 763:35-45.

What is claimed is:

1. A process for preparing an ester of mycophenolic acid, said process comprising the steps of:
   a) providing a concentrated aqueous alkaline mixture containing mycophenolic acid;
   b) admixing the mixture with a first water-immiscible solvent to form an aqueous phase and a first water-immiscible phase;
   c) separating the aqueous phase;
   d) admixing the aqueous phase with a second water-immiscible solvent at a pH of less than about 7 to form an aqueous phase and a second water-immiscible phase;
   e) separating the second water-immiscible phase;
   f) concentrating the second water-immiscible phase;
   g) crystallizing mycophenolic acid; and
   h) converting the mycophenolic acid of step (g) to an ester; wherein said ester is a morpholinoethyl ester or a $C_1$-$C_4$ alkyl ester.

2. The process of claim 1, wherein the ester is morpholinoethyl ester.

3. The process of claim 1, wherein the ester is a $C_1$ to $C_4$ alkyl ester.

4. The process of claim 1, wherein the ester is a methyl ester or t-butyl ester.

5. Mycophenolic acid in solid state having a purity of at least about 99.5% as measured by HPLC area percentage, and characterized by a powder X-ray diffraction pattern substantially as depicted in FIG. 1A or FIG. 2A.

6. The mycophenolic acid of claim 5 having a purity of at least about 99.9% as measured by HPLC area percentage.

7. Mycophenolic acid in solid state having a of total impurity content of less than about 0.1% as measured by HPLC area percentage.

8. The mycophenolic acid of claim 7 having a total impurity content of less than about 0.08% as measured by HPLC area percentage.

9. Mycophenolic acid in solid state having a melting point of about 141.6° C. to about 144.6° C., and characterized by a powder X-ray diffraction pattern substantially as depicted in FIG. 1A or FIG. 2A.

10. The mycophenolic acid of claim 9 having a melting point of about 143.1° C.

* * * * *